US011648094B2

(12) United States Patent
Reynard et al.

(10) Patent No.: US 11,648,094 B2
(45) Date of Patent: *May 16, 2023

(54) DYNAMIC DENTAL ARCH MAP

(71) Applicant: TROPHY, Croissy-Beaubourg (FR)

(72) Inventors: Delphine Reynard, Montreuil (FR); Aude Lagardere, Croissy-Beaubourg (FR); Sebastien Henry, Croissy-Beaubourg (FR); Sabrina Capron-Richard, Croissy-Beaubourg (FR); Jean-Pascal Jacob, Croissy-Beaubourg (FR)

(73) Assignee: Nobel Biocare Services AG, Kloten (CH)

( * ) Notice: Subject to any disclaimer, the term of this patent is extended or adjusted under 35 U.S.C. 154(b) by 599 days.

This patent is subject to a terminal disclaimer.

(21) Appl. No.: 16/495,075

(22) PCT Filed: Mar. 17, 2017

(86) PCT No.: PCT/IB2017/000443
§ 371 (c)(1),
(2) Date: Sep. 17, 2019

(87) PCT Pub. No.: WO2018/167530
PCT Pub. Date: Sep. 20, 2018

(65) Prior Publication Data
US 2020/0015943 A1    Jan. 16, 2020

(51) Int. Cl.
*G06T 7/12*    (2017.01)
*G06T 19/00*    (2011.01)
(Continued)

(52) U.S. Cl.
CPC .............. *A61C 9/0046* (2013.01); *G06T 7/12* (2017.01); *G06T 19/00* (2013.01); *G16H 30/40* (2018.01);
(Continued)

(58) Field of Classification Search
None
See application file for complete search history.

(56) References Cited

U.S. PATENT DOCUMENTS 8,416,984 B2    4/2013  Liang et al.
2007/0298366 A1*  12/2007  Rothstein .............. A61F 5/0006
433/19
(Continued)

FOREIGN PATENT DOCUMENTS

CN    106137414 A      11/2016
EP     2479694 A2       7/2012
WO    2015/179084 A1   11/2015

OTHER PUBLICATIONS

International Preliminary Report on Patentability received for PCT Patent Application No. PCT/IB2017/000443, dated Sep. 26, 2019, 8 pages.
(Continued)

*Primary Examiner* — Yanna Wu
(74) *Attorney, Agent, or Firm* — Alston & Bird LLP

(57) ABSTRACT

Method for automatically assigning numeric labels to teeth in a dental arch map provides a segmented 3D surface image of patient dentition having identified individual teeth and determined tooth position in the dental arch. A tooth contour for the identified teeth is defined. The tooth type is identified as one of incisor, canine, premolar, or molar. A display of the tooth contour is labeled with an assigned tooth number according to the tooth position, tooth contour, and tooth type. The labeled mapping is displayed.

20 Claims, 17 Drawing Sheets

(51) Int. Cl.
*A61C 9/00* (2006.01)
*G16H 50/20* (2018.01)
*G16H 30/40* (2018.01)
*G16H 40/63* (2018.01)
*G16H 40/67* (2018.01)
*G16H 50/50* (2018.01)

(52) U.S. Cl.
CPC .............. *G16H 40/63* (2018.01); *G16H 50/20* (2018.01); *G06T 2207/30036* (2013.01); *G16H 40/67* (2018.01); *G16H 50/50* (2018.01)

(56) References Cited

U.S. PATENT DOCUMENTS

| | | | |
|---|---|---|---|
| 2012/0189182 A1* | 7/2012 | Liang | A61C 19/00 |
| | | | 382/128 |
| 2016/0135925 A1* | 5/2016 | Mason | G16Z 99/00 |
| | | | 703/2 |
| 2017/0076443 A1* | 3/2017 | Ye | A61C 7/002 |
| 2017/0169562 A1* | 6/2017 | Somasundaram | G06V 20/653 |
| 2018/0078347 A1* | 3/2018 | Falkel | A61B 1/000094 |
| 2019/0216545 A1* | 7/2019 | Piron | A61B 34/10 |

OTHER PUBLICATIONS

International Search Report and Written Opinion received for PCT Patent Application No. PCT/IB2017/000443, dated Nov. 27, 2017, 11 pages.

* cited by examiner

US 11,648,094 B2

DYNAMIC DENTAL ARCH MAP

FIELD OF THE INVENTION

The disclosure relates generally to imaging methods and apparatus and more particularly to methods and apparatus that generate a two-dimensional map of the dental arch from three-dimensional surface information about the patient.

BACKGROUND OF THE INVENTION

The conventional dental chart or dental arch map is used to assist the practitioner and larger dental team, providing a vehicle for organizing annotation and other information related to tooth condition and treatment for each particular patient. In conventional practice, the same basic dental chart is used as a starting point for each patient. Using this mapping of the dental arch as a reference, diagnostic assessment and treatment procedures can proceed and can be correlated to each tooth as needed. Dental charts are complex, intricate and contain large amounts of data per patient. See for example, U. S. Pat. No. 8,416,984 entitled "Automatic tooth charting using digital images".

The dental arch map that is conventionally used, however, is a standard mapping arrangement and may not apply equally well to each patient.

There are a number of conditions that can render the standard dental arch map as incorrect or confusing for an individual patient and can tend to complicate the use of a standard mapping of tooth structures. Patient conditions that can compromise the effectiveness of the standard dental chart include cases of poor alignment, missing teeth, supernumerary teeth, and tooth arrangements with a mixing of permanent and deciduous teeth, for example.

It can be appreciated that there would be advantages to apparatus and methods for generating a dental chart that accurately represents the actual tooth arrangement of each individual patient.

SUMMARY OF THE INVENTION

It is an object of the present disclosure to advance the art of diagnostic imaging and to address the need for generating a dental chart having an arch mapping that accurately represents the dentition of an individual patient. An embodiment of the present disclosure processes 3D tooth contour information available from a dental imaging apparatus to automatically generate a 2D dental arch map for the patient.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to an aspect of the present disclosure, there is provided a method for generating a dental arch map for a patient that can include acquiring a 3D surface image of patient dentition, automatically segmenting the 3D surface image to identify individual teeth, forming a mapping of outlines for the identified teeth, and displaying the labeled mapping. In one exemplary embodiment, the mapping can be automatically labeled according to a designated tooth numbering scheme.

According to an aspect of the present disclosure, there is provided a method for automatically assigning numeric labels to teeth in a dental arch map comprising:

providing a segmented 3D surface image of patient dentition comprising identified individual teeth and determined tooth position in the dental arch;

defining a tooth contour for the identified teeth;

identifying the tooth type as one of incisor, canine, premolar, or molar; labeling a display of the tooth contour with an assigned tooth number according to the tooth position, tooth contour, and tooth type; and displaying the labeled mapping.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be useful in order to emphasize basic structural relationships, operator interface capabilities, or principles of operation.

DESCRIPTION OF EXEMPLARY EMBODIMENTS

Figure 1:
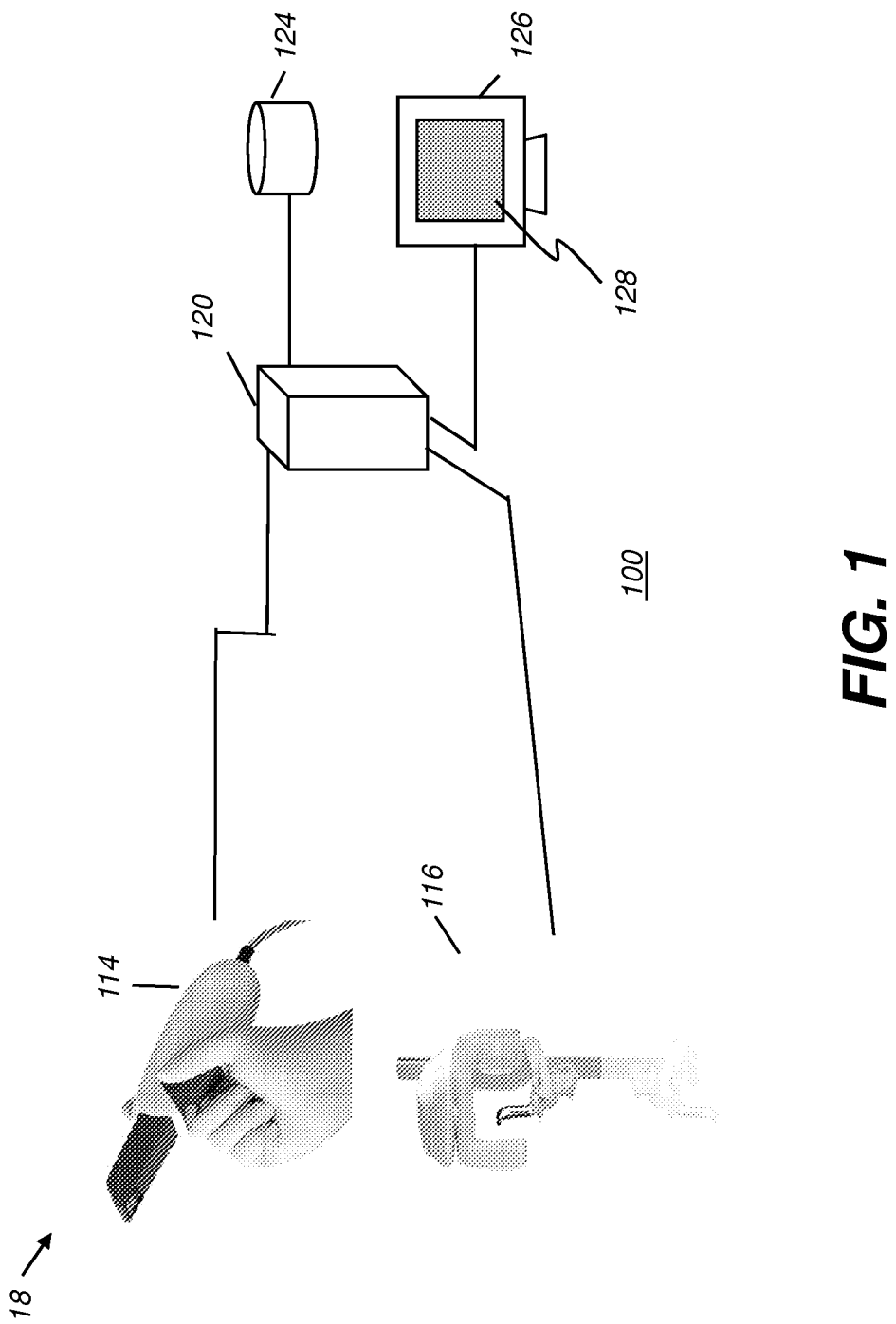
FIG. 1 shows components of a dental imaging system for obtaining and displaying patient images of various types, including images acquired during different stages of a treatment session.

The following is a description of exemplary method and/or apparatus embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the terms "viewer", "operator", and "user" are considered to be equivalent and refer to the viewing practitioner, technician, or other person who may operate an imaging system, camera, or scanner and may also view and manipulate the presentation of an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "imaging apparatus" relates to a device that is enabled to acquire any of a number of types of images, using an appropriate source of light energy or radiation, including various types of reflectance imaging, structured light imaging, panoramic imaging, x-ray imaging, computed tomography (CT) imaging, cone beam computed tomography (CBCT) imaging, optical coherence tomography (OCT) or other imaging type.

The term "subject" refers to the tooth or other portion of a patient that is imaged and displayed. The terms "3D image", "3D surface", "surface contour image", or "volume image" are used equivalently.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual tooth, organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

FIG. 1 shows components of a dental imaging system 100 for obtaining and displaying patient images of various types, including images of patient dentition acquired during different stages of a treatment session. Dental imaging system 100 includes at least one imaging apparatus 18 for 3D surface image acquisition, which may be a digital camera 114 such as an intra-oral camera or scanner, such as a structured light imaging scanner using reflectance imaging, or a dental cone-beam computed tomography (CBCT) system 116 for generating volume images of tooth surface and related structure. Other types of imaging apparatus 18 could also be employed for obtaining images of teeth and supporting structures, gums, and related tissue, such as panoramic imaging apparatus, or ultrasound imaging apparatus. In addition, various types of diagnostic measurement instrumentation may also be provided for working with dental imaging system 100, as described in more detail subsequently.

Still referring to FIG. 1, a host processor 120, such as computer(s) or other type of dedicated logic processor for obtaining, processing, and storing image data from the imaging apparatus 18 is also part of dental imaging system 100, along with one or more displays 126 for viewing image results. Each display 126 can have a graphical user interface (GUI) 128 for entry of viewer instructions. GUI 128 can use a touch screen or other instruction entry device, such as a mouse or other pointer. Host processor 120 is in data and signal communication with one or more image capture devices for image acquisition and, optionally, with any number of automated measurement devices (not shown in FIG. 1). In addition, host processor 120 can also be in data and signal communication with a database of patient records, stored internally or on a networked host or server (not shown), which can be provided locally or remote, for example. A computer-accessible memory 124 is also provided, which may be a non-volatile memory storage device used for longer term storage, such as a device using magnetic, optical, or other data storage media. In addition, computer-accessible memory 124 can comprise a volatile electronic memory such as a random access memory (RAM), within or otherwise in data communication with host processor 120, that is used for shorter term data storage, such as memory used in conjunction with a display device for temporarily storing image content as a display buffer, or memory that is employed to store a computer program having instructions for controlling one or more computers to practice the method according to the present disclosure.

Figure 2:
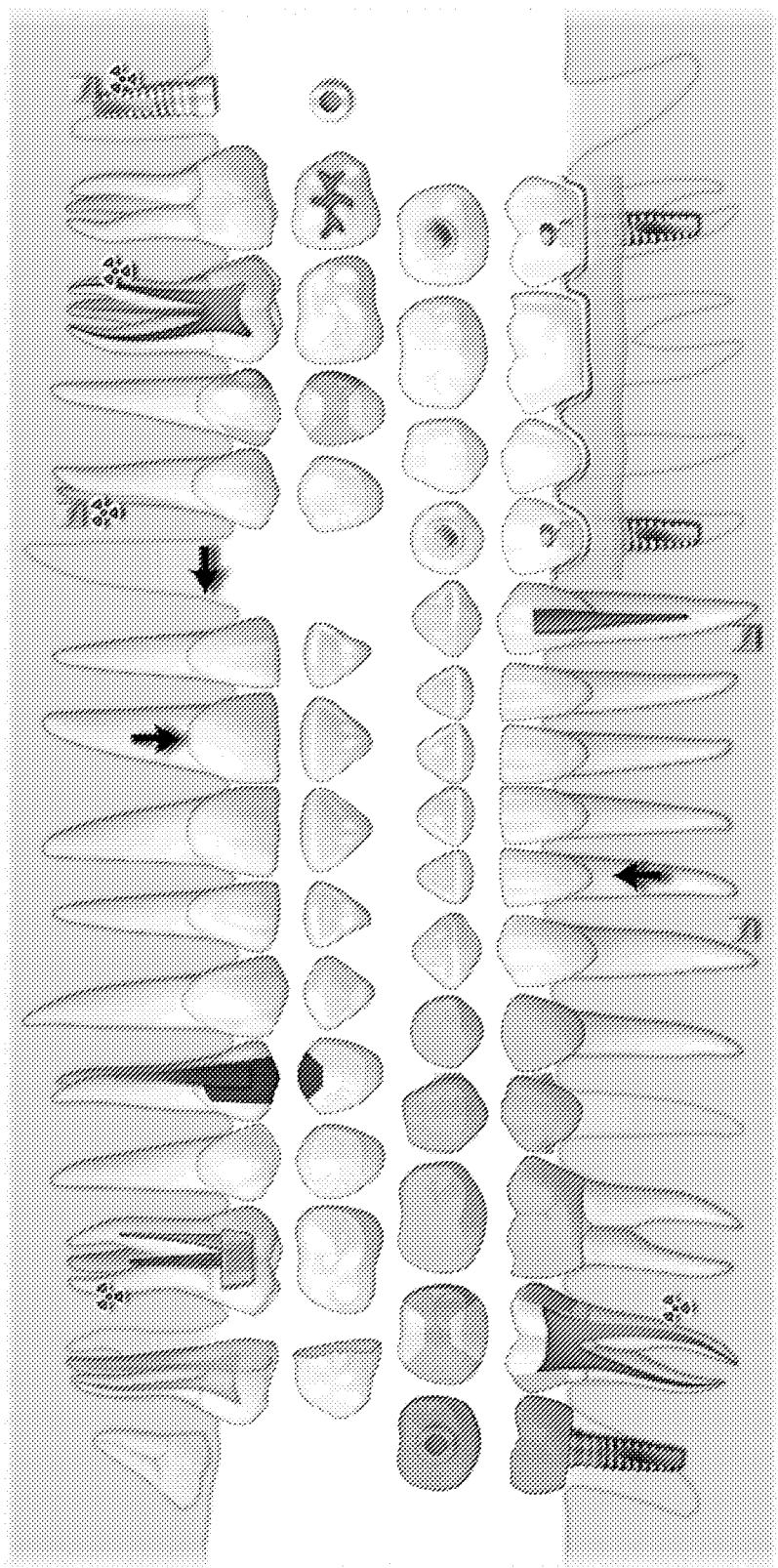
FIG. 2 shows a standard arrangement of maxillary and mandibular arches for a patient.

FIG. 2 shows one type of conventional dental chart showing a standard arrangement of views of maxillary and mandibular arches for a patient. As described previously, one or more of the teeth may be missing, misaligned, or supernumerary to the standard dental arch arrangement for a particular patient. Supernumerary teeth can be particularly difficult.

Figure 3:
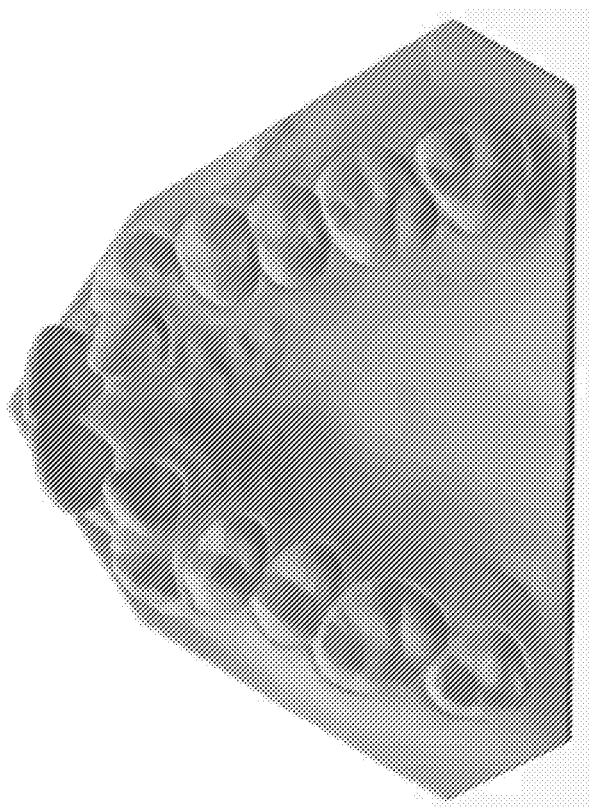
FIG. 3 shows maxillary arch dentition for an exemplary patient, as scanned from an impression.

FIG. 3 shows maxillary arch dentition for a particular patient, as scanned from an impression or using an intraoral camera, for example. As can be readily seen, this arch exhibits an irregular tooth pattern. It would be difficult to accurately represent the arrangement of teeth shown to the standard dental arch arrangement of FIG. 2 or to another type of conventional dental chart.

Figure 4:
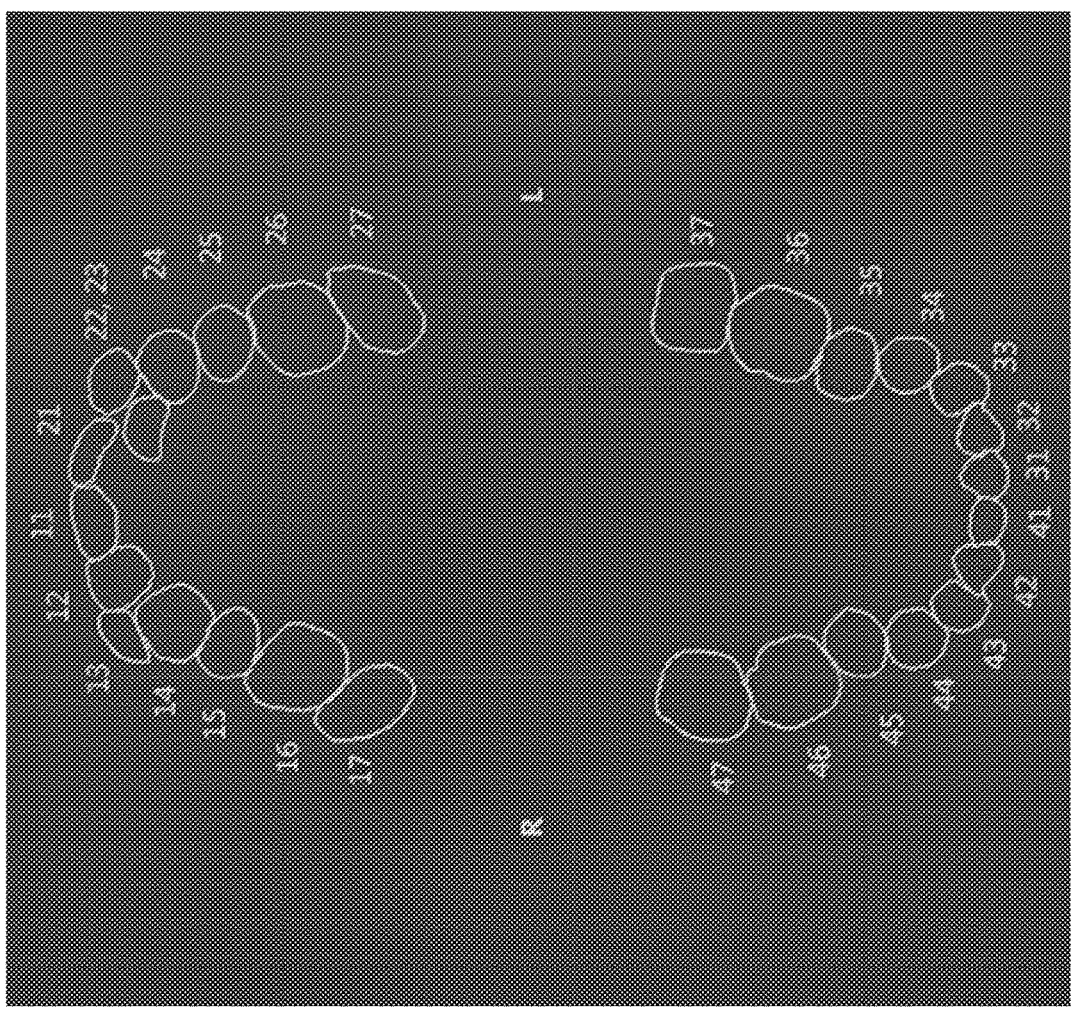
FIG. 4 shows an exemplary 2D dental arch map embodiment obtained from a 3D surface contour image according to the application.

FIG. 4 shows an exemplary dynamic 2D dental arch map obtained from 3D images according to method and/or apparatus embodiments described herein. Tooth numbering can be provided for the teeth in each arch. Irregular teeth are mapped and numbered for reference in providing annotation to support diagnosis and treatment of each tooth.

Figure 5:
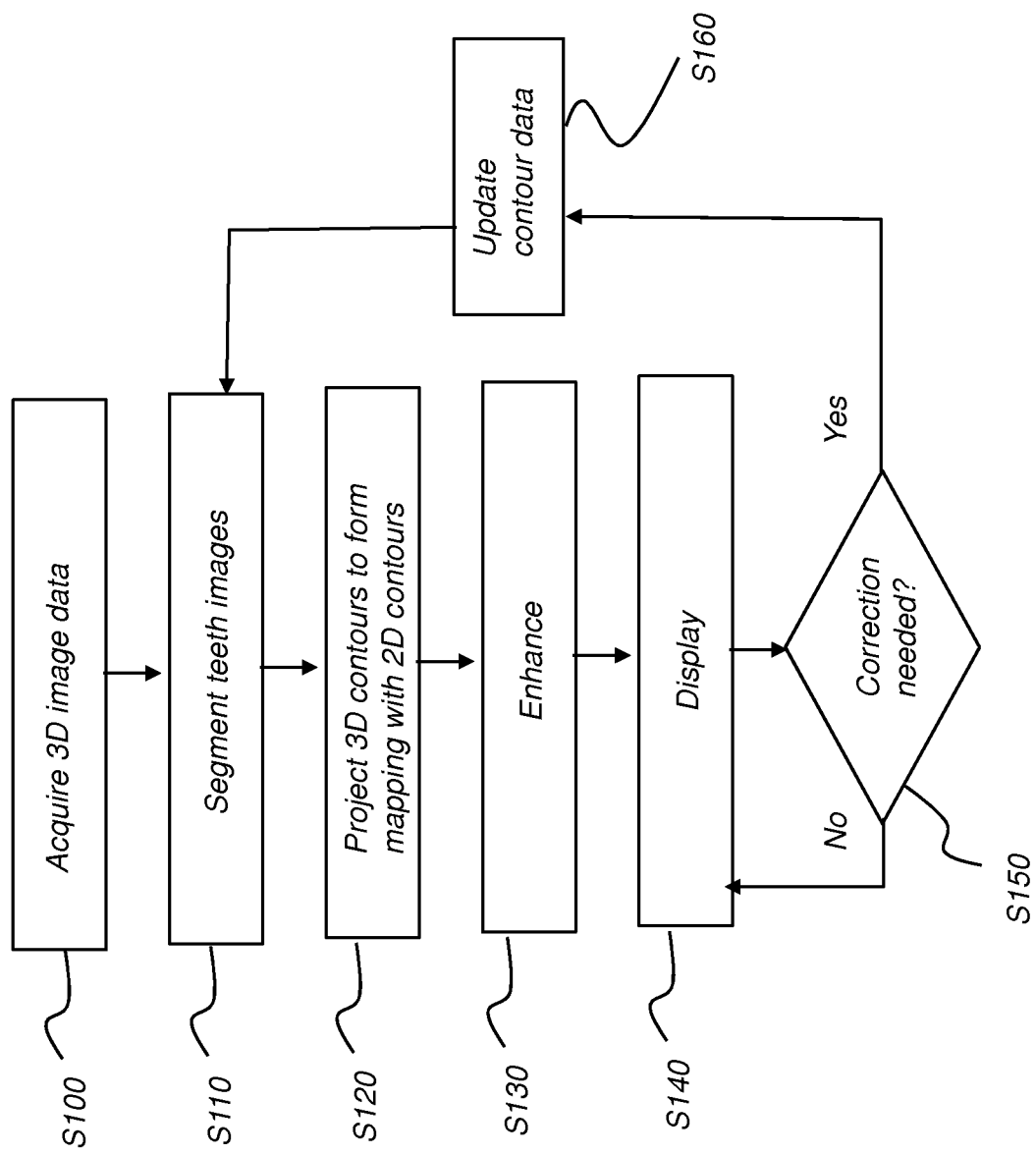
FIG. 5 is a logic flow diagram that shows exemplary dental arch map generation and updating method embodiments according to the application.

The dental arch map of FIG. 4 can be generated from the 3D surface image data in a number of ways. FIG. 5 shows a logic flow diagram that describes exemplary steps for dental arch map generation and updating according to certain exemplary embodiments of the application. This processing can be performed, for example, using the processor 120 and imaging apparatus described previously with reference to FIG. 1. In a volume image acquisition step S100, a 3D surface image of the patient teeth is obtained from an image source, such as one of the surface imaging sources described previously with respect to FIG. 1. The 3D image content can be obtained from a CBCT system, for example, providing full volume or 3D surface image data obtained by reconstruction from a sequence of radiographic images obtained at different angles of the radiation source and detector, using 3D volume reconstruction methods familiar to those skilled in the volume imaging arts. The images can be obtained by scanning the patient or by scanning an impression of the patient's dentition. Alternately, the image content can be from 3D surface imaging obtained using an intra-oral camera using structured light techniques. The 3D surface image content can include any portion of the dental arch or the entire dental arch of the patient.

Figure 6:
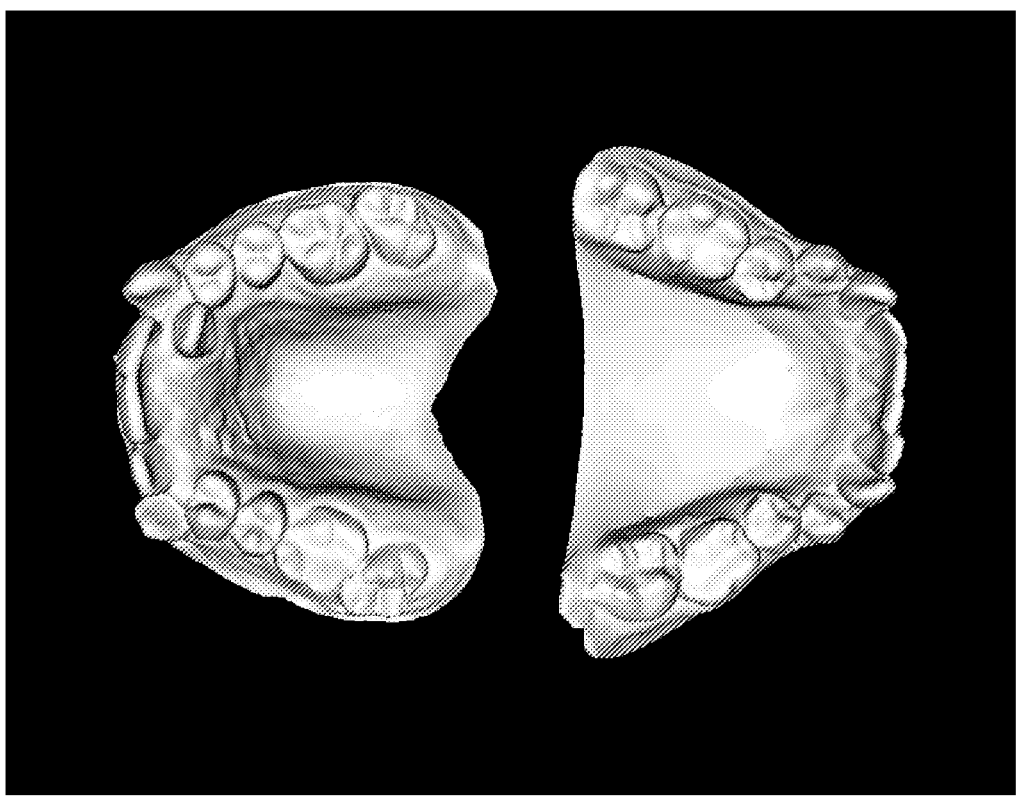
FIG. 6 shows contour image content obtained using the imaging apparatus of FIG. 1.

Referring to FIG. 6, there is shown an example display of dentition 3D surface image content for both upper and lower arches. FIG. 6 shows, in modeled form, 3D surface image content that can be obtained from the imaging apparatus of FIG. 1. In one embodiment, the example display of 3D surface image content for both upper and lower arches in FIG. 6 can result from step S100.

In a segmentation step S110, the 3D image content is processed in order to define the contour boundaries of the individual teeth. Segmentation processing can be fully automated or can be manually assisted in some way, such as by the entry of seed data or other initialization data. Methods that can be used for segmentation include snake-based segmentation, iterative segmentation techniques, region growing, and other techniques well known to those skilled in the image processing arts. Full segmentation of the tooth volume may not be required for forming a dental arch map. For example, a top view that can define the contour image of each tooth may be sufficient for generating a dental arch map that characterizes the arch for a particular patient.

Once the teeth are successfully segmented, a projection step S120 executes, in which the defined 3D contours are projected along a 2D plane to form the 2D contours or outlines of the dental arch map. Projection step S120 can be performed in any of a number of ways. According to an exemplary embodiment of the present disclosure, the 3D cervical margin boundaries can be projected into the same (e.g., Z=0) plane (that is, projected onto the same plane for all the models). Based on the initial orientation of the model, however, some projections could have artifacts and may poorly represent the tooth. Alternately, a best plane that limits such artifacts can be determined, using the occlusal plane axis of the model or the orientation axis of each tooth. For example, the axis of each tooth can be identified, which increases or maximizes the area of the projected contour. Weighting could be applied, with a higher weight assigned for incisors or other teeth based on factors such as ease of detection. Alternately, an axis that reduces or minimizes 2D tooth intersections between tooth outline boundaries can be used. The projection axis can alternately be adapted or modified, tooth by tooth, or according to tooth type (such as using a different projection axis for incisor, canine, premolar, and molar teeth).

Figure 7A:
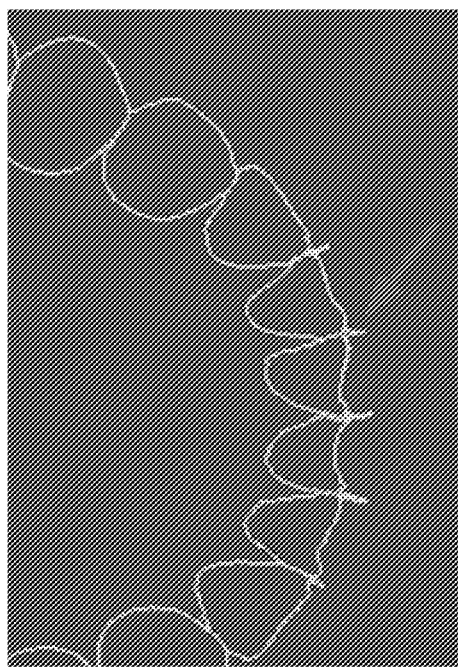
FIGS. 7A and 7B show different projections for forming a 2D dental arch map.
Figure 7B:
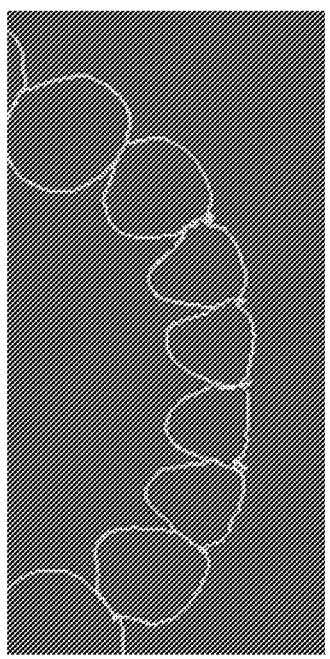

FIGS. 7A and 7B show an exemplary projection used for forming outlines of the 2D dental arch map. FIG. 7B shows correction of the 2D projections for slight inaccuracy in tooth outline boundaries shown for tooth separation in FIG. 7A.

Referring again to the FIG. 5 sequence, in an enhancement step S130, teeth can be labeled using a tooth numbering scheme. Tooth numbering can follow any suitable standard as a tooth numbering scheme, including the Universal Numbering System, International Standards Organization (ISO) Designation System numbering (ISO 3950), and Palmer notation, for example, described in more detail subsequently. Tooth numbering can be automated or manual, with editing utilities available for operator correction using the graphical user interface. Automated numbering can use reference templates or models of standard patient dentition stored as part of the system software. For example, multiple models of standard dentition can be stored according to patient sex, age, size, and other factors. As another part of enhancement step S130, the obtained 2D contours can be smoothed to enhance visibility or readability, such as using a smoothing filter or by finding the convex envelope for each contour. Where one 2D contour outline intersects with another, it can be possible to slightly move or to dimensionally reduce the contours to reduce or prevent obstruction or overlap in dental arch mappings.

Editing of the cervical margin or other tooth contour definitions can also be performed as part of enhancement step S130 in the FIG. 5 sequence. Editing operations can alternately be performed on the outline or margin lines, the tooth labels, or the mesio-distal orientations, for example. Some of the exemplary editing functions that can be used include creation of the outline, editing, deletion, label change, and orientation adjustment. For interactive editing by the practitioner or technician, the tooth outline can be selected using a touch screen instruction or using a mouse or other pointer to specify the particular tooth on the outline display of the dental arch (e.g., using the exemplary 2D dental arch map shown in FIG. 4). The selection of a particular tooth in the dynamic dental arch map can cause the selected outline or cervical margin line(s) to be highlighted within the dental arch model, with focus on the selected tooth outline for image manipulation features such as automatic zoom, pan, and rotation for the tooth or for its surrounding region. Highlighting can be provided using color, reinforced outlining, or bold lines, for example.

As the operator edits existing cervical margins or other tooth data on the displayed dynamic dental arch map, the outline of the tooth can be recomputed, the dental arch map updated, and the edits shown in the newly presented map.

Continuing with the sequence of FIG. 5, results of the dynamic dental arch map processing are displayed to the practitioner in a display step S140. In addition, the teeth labels can also display in the map, such as positioned within or just outside the tooth outline.

In some cases, the practitioner may examine the volume image and may see the need to correct information about one or more teeth, where this added information may require consequent update of the dental map. In one embodiment, the imaging system is alerted to this type of condition in a test step S150. Where update or adjustment is made, an update step S160 executes. Processing then returns to segmentation step S110 and steps S120 and S130 for generating the new mapping based on updated information. Operator instructions can identify one or more teeth that were not detected by automated segmentation procedure, for example. In certain exemplary embodiments, step S150 can be implemented in a GUI using selectable controls including edit map/approve map actions. Alternatively, dialog window process can implement step S150. In one embodiment, steps S150 and S160 are optional.

As described herein, the dental arch map that is generated is correlated to the virtual model data. Any action performed on the dental arch map is automatically reflected in the 3D scene. Similarly, changes in the 3D scene are shown on the dental arch map according to exemplary embodiments.

Figure 8A:
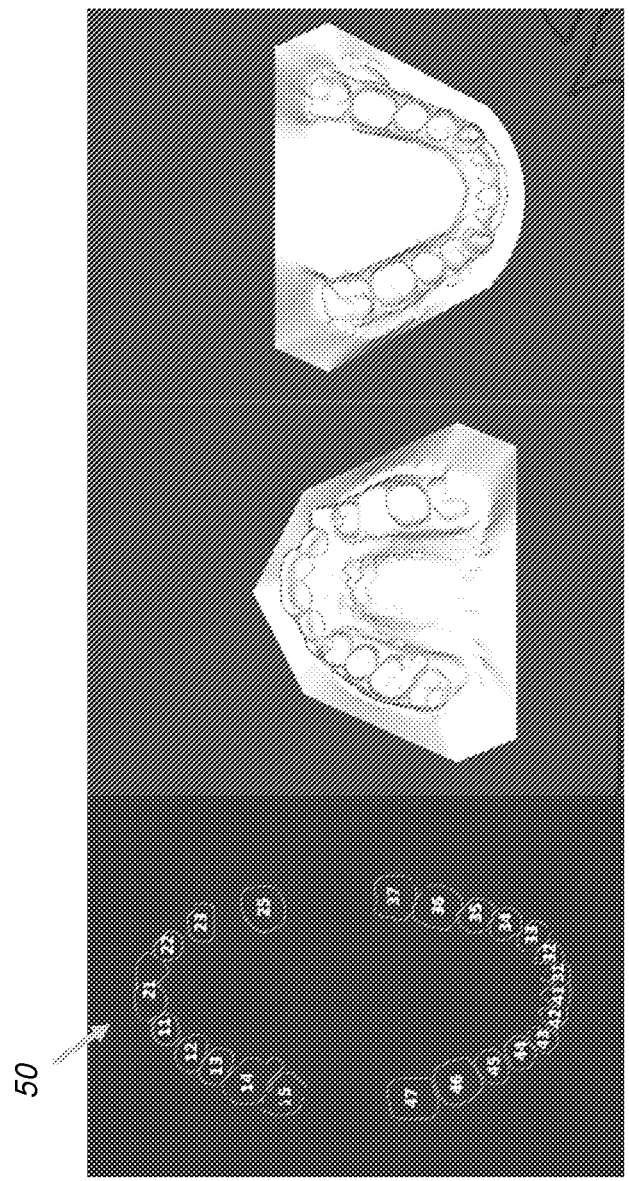
FIG. 8A shows generation of a dental arch map from 3D volume information obtained from scanned impressions.

FIG. 8A shows generation of an exemplary complete dental arch map 50 from 3D surface information obtained from scanned impressions of a patient. Successfully segmented teeth are highlighted, outlined in the reconstructed volume image that displays. Note that the tooth numbered 24 is missing from the upper arch, for example, and that not all teeth appear to be correctly segmented.

Figure 8B:
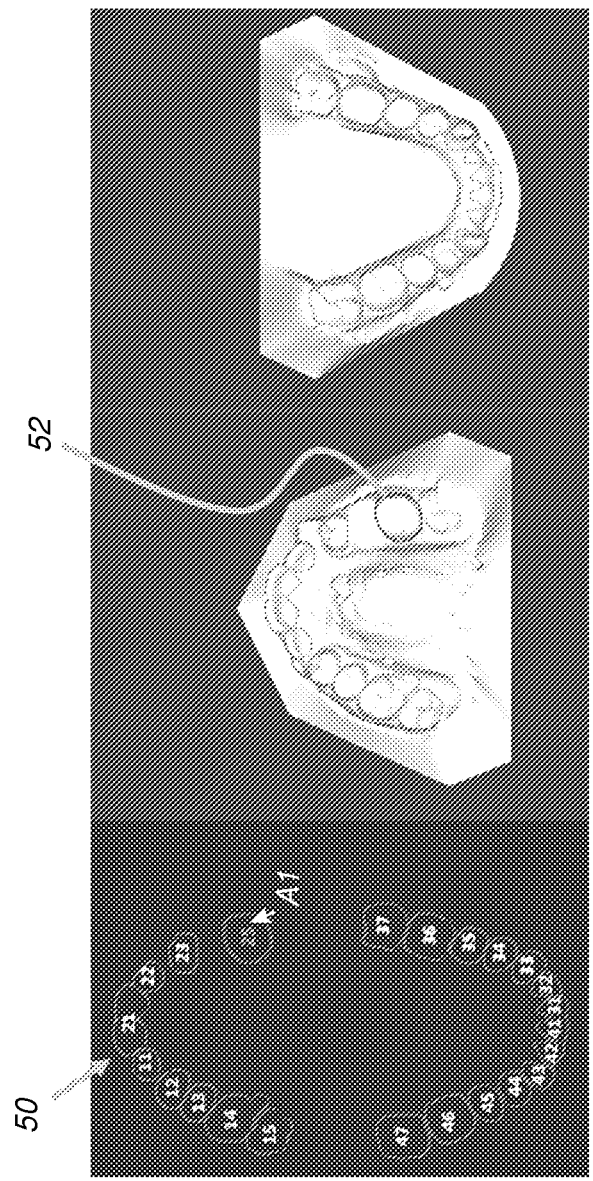
FIG. 8B shows correction of a tooth outline from the generated dental arch map of FIG. 8A.

FIG. 8B shows correction of a tooth outline for the tooth numbered 25 in the generated dental arch map 50. The corresponding element, tooth crown 52, in the 3D scene is highlighted as the outline for tooth numbered 25 (arrow A1) is edited.

Figure 9:
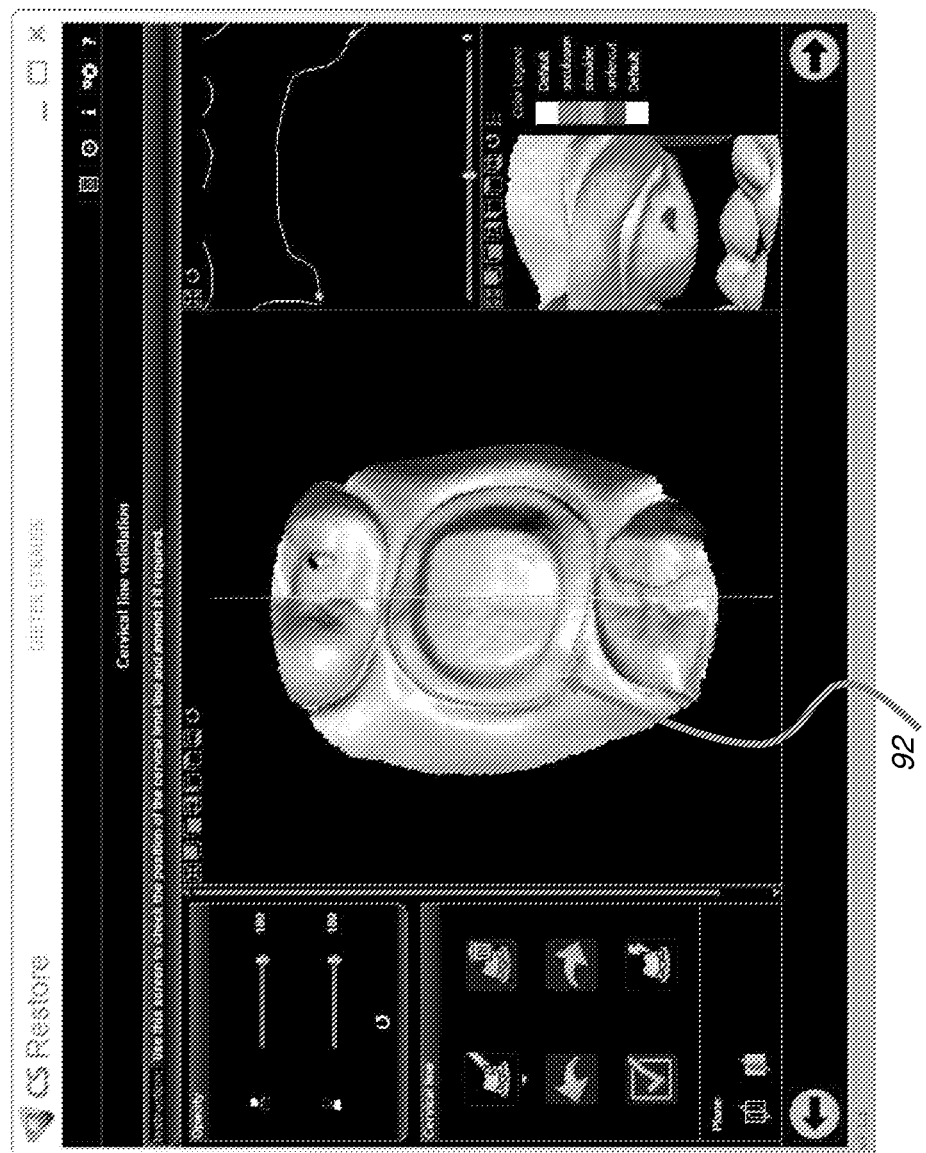
FIG. 9 shows a close-up view of an editing function that can correct or adjust for errors that relate to one or more elements of dental map.

FIG. 9 shows a close-up view of an exemplary editing function embodiment that can be used to correct or adjust for errors that relate to outlines or other features of one or more tooth elements of the dental map. In the example shown, re-shaping of a cervical minimum 92 in the 3D scene can help to provide an improved outline representation and characterization of the tooth. Highlighting one or more of the outlines in the mapping and recomputing the one or more highlighted outlines according to operator instructions can also be performed.

Figure 10:
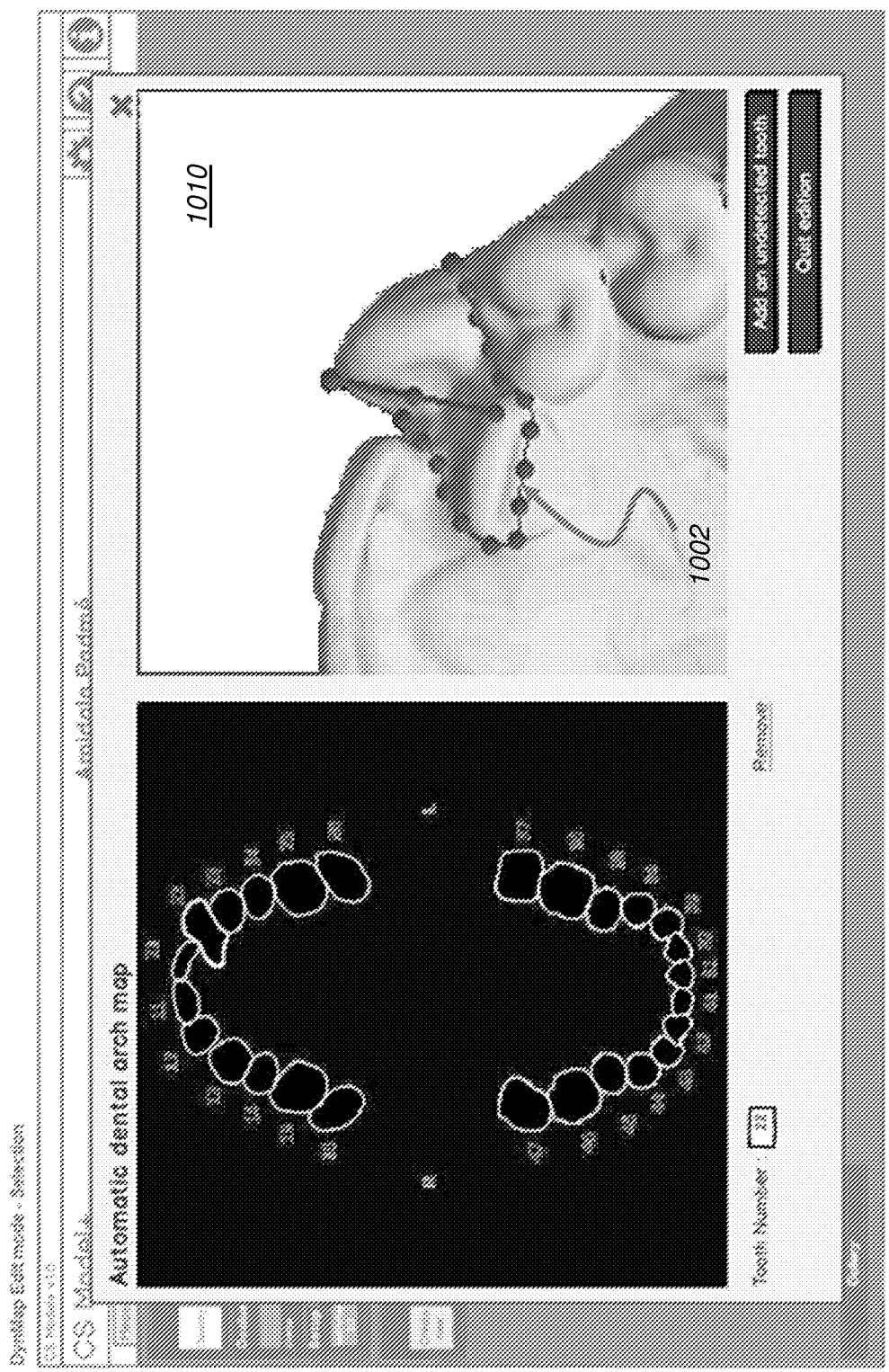
FIG. 10 shows editing of the arch map for teeth that have not been properly identified using automated segmentation.

FIG. 10 shows another exemplary editing function of the dental arch map for teeth that have not been properly identified using automated segmentation. The practitioner or other operator can correct for segmentation discrepancies using manual markup commands entered on the display screen. For the example shown in FIG. 10, irregular tooth spacing is corrected using a manual markup sequence, then segmentation can be re-initiated in order to recompute tooth outline and boundaries. For the example shown in FIG. 10, irregular tooth spacing is corrected at 1002 in a corresponding 3D scene 1010. An operator instruction can be entered to retry segmentation for teeth not detected or processed in previous steps.

Figure 11:
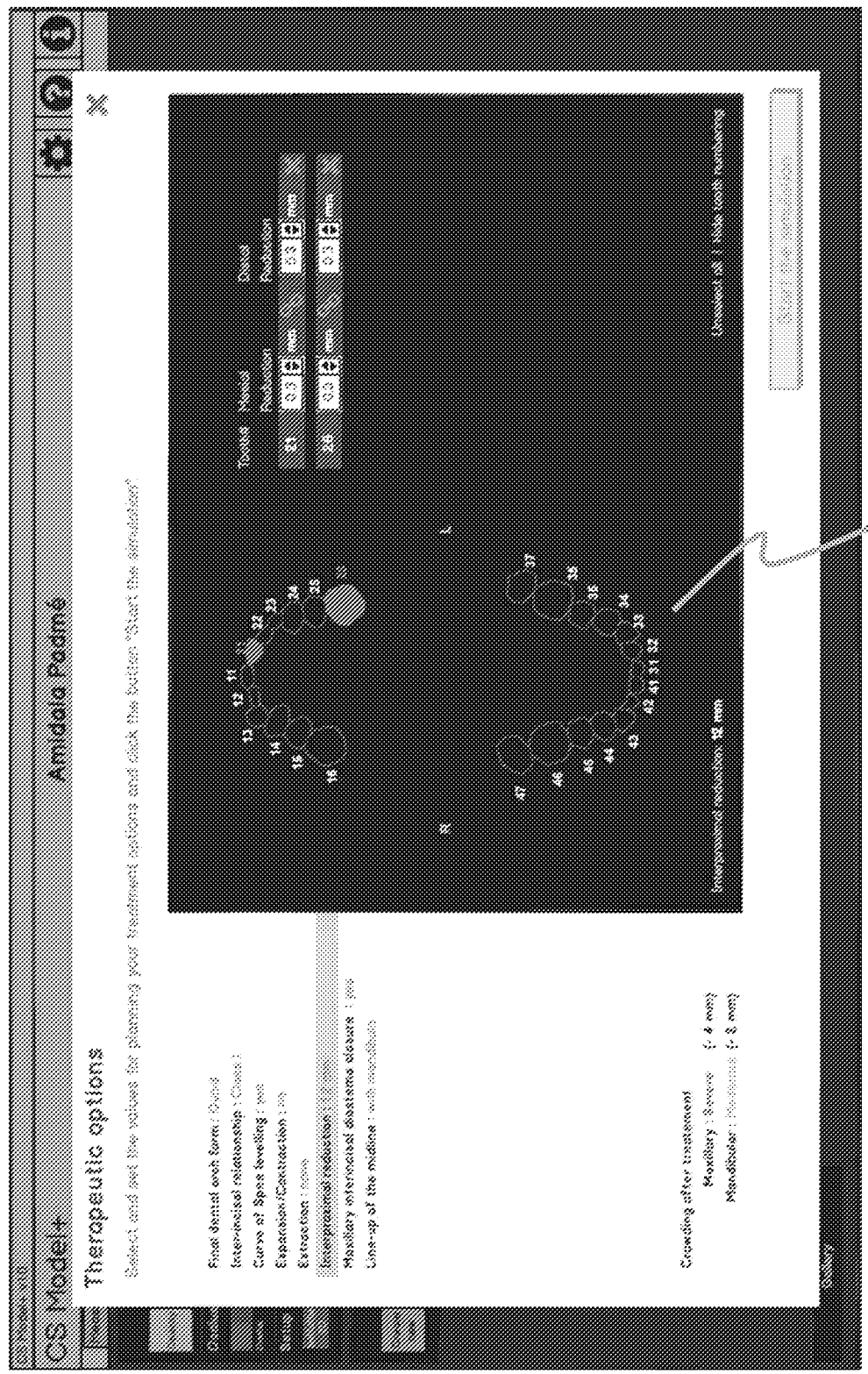
FIG. 11 shows the use of the dynamic dental arch map with simulation for selected teeth.

FIG. 11 shows the use of the dynamic dental arch map 50 with simulation software for manipulating content for selected teeth. The viewer can specify one or more teeth for simulation, such as by clicking or otherwise selecting teeth from the arch map 50, then show the appearance of the dental arch map 50 with the simulated action taken, such as with planned or contemplated tooth removal, adjustment to alignment, or re-spacing, for example.

Because it uses 3D volume information acquired from the patient, the dental arch map of the present disclosure can be more accurate for planning and tracking individual progress than are conventional dental arch mapping tools. The dental arch map that is generated using the sequence of FIG. 5 can be used not only for forming a treatment plan, but also for helping to visualize planned changes in the dental arch with ongoing treatment. According to an exemplary embodiment of the present disclosure, the individual tooth outlines provided on the dynamic dental arch map can serve as indices for access to additional images and annotation for the teeth. Thus, in some exemplary embodiments, the dynamic dental arch map 50 can be used with various dentist/dental functions. For example, selecting a particular tooth on the display can enable selective display of images of the tooth as well as records and annotation for previous or planned treatment of the tooth.

A 3D image can include surface contour image content that provides data for characterizing a surface, such as surface structure, curvature, and contour characteristics, but is not able to provide information on material that lies below the surface. Alternate techniques for contour imaging such as dental contour imaging can include structured light imaging using visible light, near-infrared light, or ultraviolet light wavelengths as well as other known techniques for characterizing surface structure, such as feature tracking by triangularization, structure from motion photogrammetry, time-of-flight imaging, and depth from focus imaging, for example. Contour image content can also be extracted from volume image content, such as by identifying and collecting only those voxels that represent surface tissue, for example.

Dental Tooth Numbering Systems

An embodiment of the present disclosure allows the operator to select from any of a number of dental tooth numbering systems, including well-established standard systems.

One widely used numbering system that is a standard for labeling teeth is the Palmer notation method, also known as the Zsigmondy or Grid system. Quadrant-based, the Palmer method counts outward from the center teeth in each quadrant of the mouth. For permanent teeth, numbering within each quadrant is in the range 1 through 8, with accompanying symbols that indicate the quadrant position. Deciduous teeth are labeled using capital letter A through E in each quadrant.

The Universal Numbering System, also known as the American system, assigns numeric labels with the number 1 assigned as label to the upper molar at the right side of the patient and successive numbering advancing along the upper teeth, to the third molar on the upper left side, assigned number 16. The molar beneath number 16 is labeled number 17, with numbering continued to 32 as the last lower molar on the right side below number 1. Deciduous teeth are labeled using capital letters A-T. Letter D designates the upper first tooth on the right side. Letter T is assigned as label to the last tooth on the lower right side.

The ISO system, also known as ISO 3950, uses a 2-digit label for each tooth. The first digit is a quadrant reference; the second digit labels the tooth within the quadrant. Individual teeth are labeled from 1-8 starting from the center teeth. Quadrant numbering is from 1 to 4 for permanent teeth; numbers 5 to 8 are used to label primary teeth, wherein the upper right is 1, upper left 2, lower left 3, and lower right 4. A similar pattern applies for deciduous teeth using the ISO labeling system.

According to an embodiment of the present disclosure, supernumerary teeth are labeled appropriately for whatever dental tooth numbering system has been selected.

Use of Labeling in an Imaging System

Figure 12:
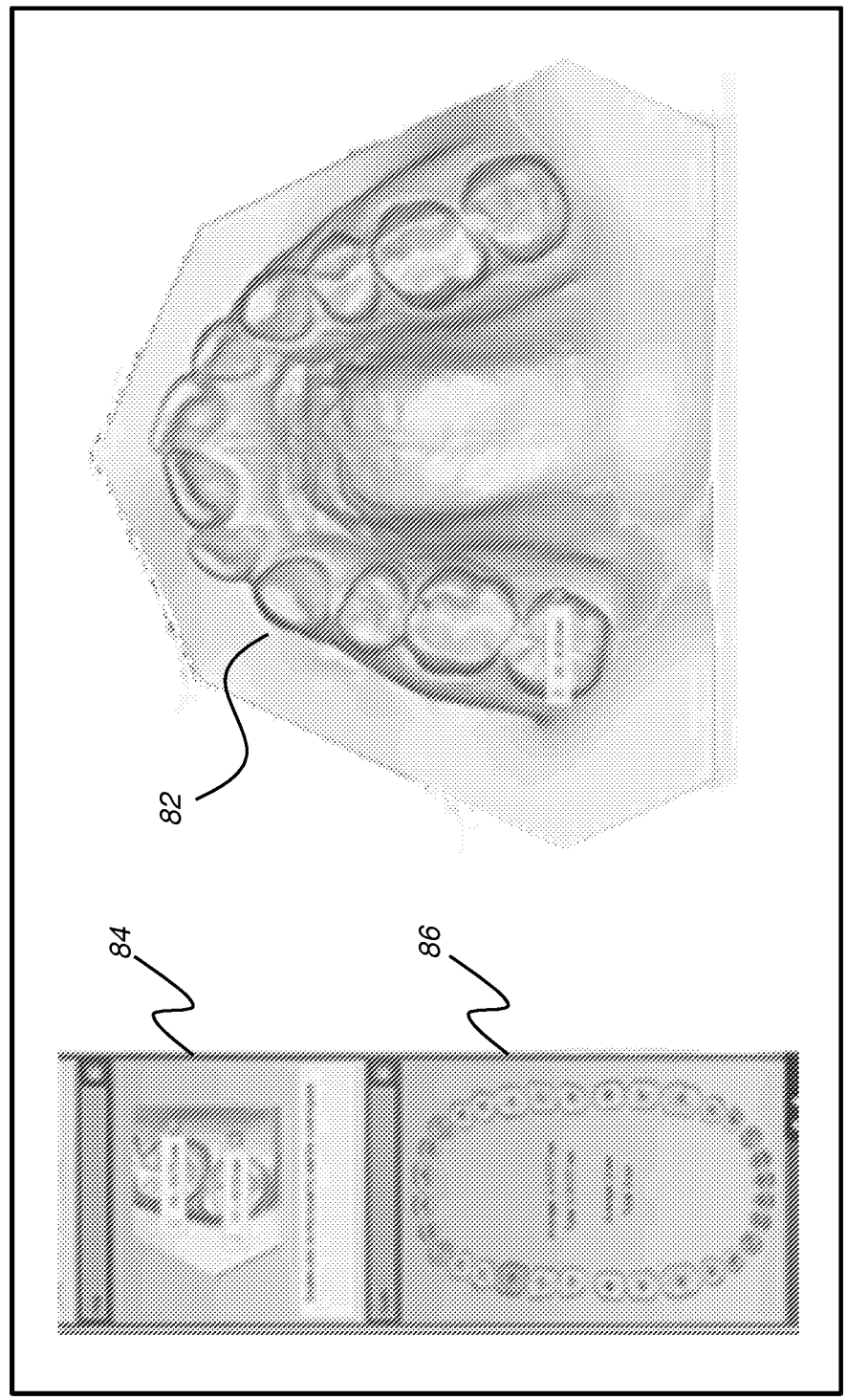
FIG. 12 is an example of a user interface that employs a dental chart with automatic tooth labeling.

The exemplary graphical user interface (GUI) 78 of FIG. 12 shows how dental numbering can be used for labeling a visual representation based on a mesh or other volume image for a displayed dental arch 82. The practitioner can select a particular numbered tooth from the dental arch 82 display in order to show more detailed information, such as in another on-screen window 84. Selection can be performed using an interface utility such as a mouse or touch screen. A labeled chart 86 shows the assigned numbers used as labels for the corresponding teeth.

Sequence for Automated Label Assignment

As was noted previously, the task of numbered label assignment can be complicated by various factors, including an irregular or transitional arrangement of tooth features. For example, in orthodontic practice for younger patients, it can be difficult to automatically detect and properly label deciduous teeth and to distinguish these from permanent teeth. Embodiments of the present disclosure address the problem of automated tooth numbering, also termed tooth labeling, using the segmented 3D mesh or other volume image provided by a dental imaging apparatus, as described previously.

Figure 13:
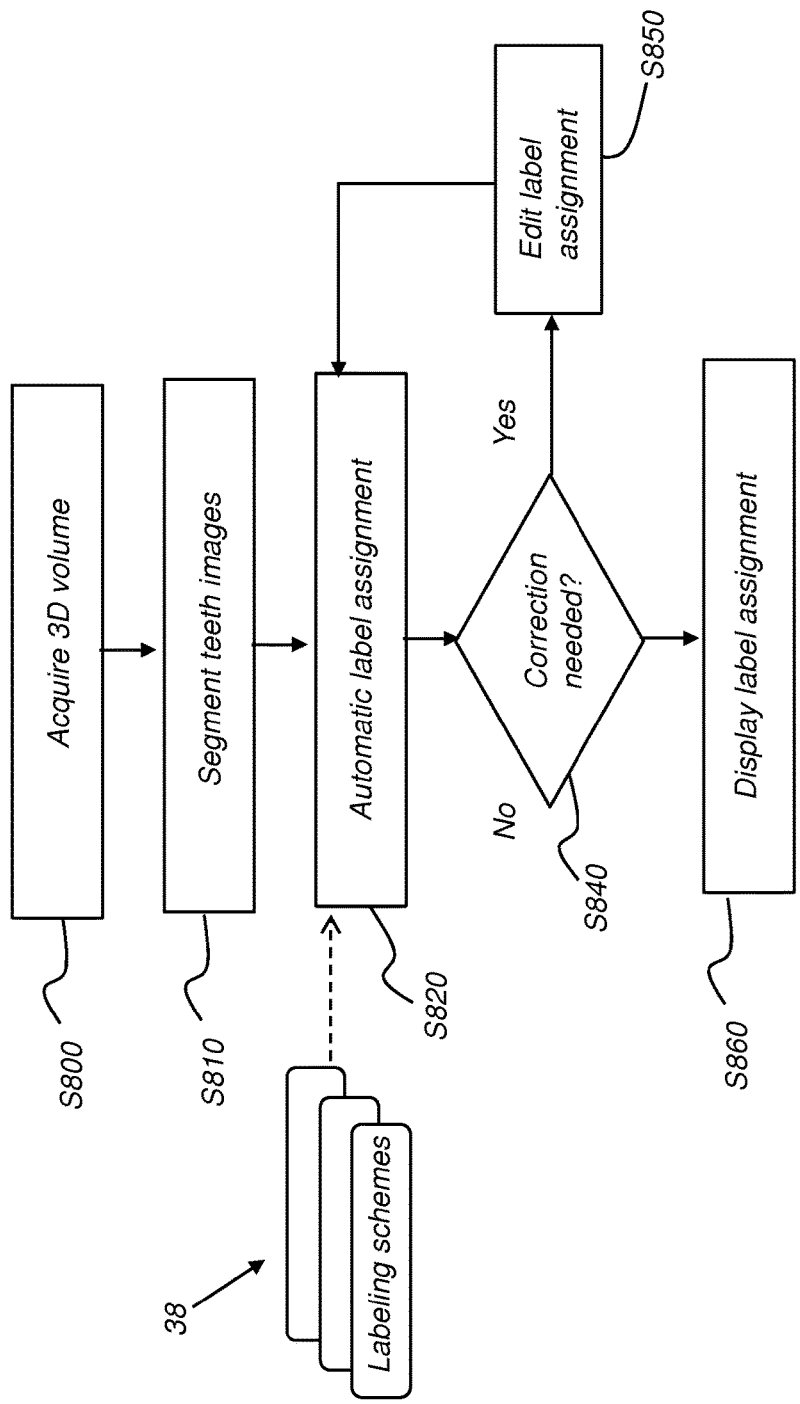
FIG. 13 is a logic flow diagram that shows a sequence for automatic tooth numbering according to an embodiment of the present disclosure.

FIG. 13 is a logic flow diagram that shows a sequence for automatic tooth numbering according to an embodiment of the present disclosure. Processing begins with a volume acquisition step S800, in which a 3D volume formed from tomographic reconstruction or a mesh is generated from point cloud image content, obtained from an intraoral scanner or CBCT system as described previously. The 3D image content used to generate the mesh can be obtained from a CBCT system, for example, providing full volume or 3D surface image data obtained by reconstruction from a sequence of radiographic images obtained at different angles of the radiation source and detector, using 3D volume reconstruction methods familiar to those skilled in the volume imaging arts. The images can be obtained by scanning the patient or by scanning an impression of the patient's dentition. Alternately, the image content can be from 3D surface imaging obtained using an intra-oral camera using structured light techniques. The 3D surface image content can include any portion of the dental arch or the entire dental arch of the patient.

A segmentation step S810 provides the segmentation results that distinguish separate teeth within the volume data. In a segmentation step S810, the 3D image content is processed in order to define the contour boundaries of the individual teeth. Segmentation processing can be fully automated or can be manually assisted in some way, such as by the entry of seed points or features or other initialization data. Editing of automated segmentation can also be provided. Any of a number of methods can be used for segmentation, including snake-based segmentation, iterative segmentation techniques, region growing, and other techniques well known to those skilled in the image processing arts. Full segmentation of the tooth volume may not be required for forming a dental arch map; a top view that can define the contour image of each tooth may be sufficient for generating a dental arch map that characterizes the arch for a particular patient.

An automatic label assignment step S820 then generates the tooth number that is assigned as a label for each tooth. One of a set of available labeling schemes 38 can be used for automated tooth labeling, such as the Palmer, ISO, or Universal schemes noted previously. An operator check step S840 enables the practitioner or other operator to indicate to the system whether or not correction is needed for one or more label assignments. An editing step S850 allows the practitioner or other operator to manually edit the automated label assignment and provide correct tooth numbering for one or more teeth. Editing can be performed using standard user interface utilities to identify the labeling to be changed, such as using a touch screen or mouse click, and to edit one or more digits of the assigned label using a keyboard or on-screen keypad. A display step S860 then displays the dental arch map with automated tooth numbering assignments and can also provide storage and transmission of the dental arch map with tooth numbering data.

It should be noted that the procedure shown in FIG. 13 can be used for numbering over the complete maxillary or mandibular arch or over just a selected portion of the arch.

Detailed Steps for Numeric Label Assignment

Figure 14:
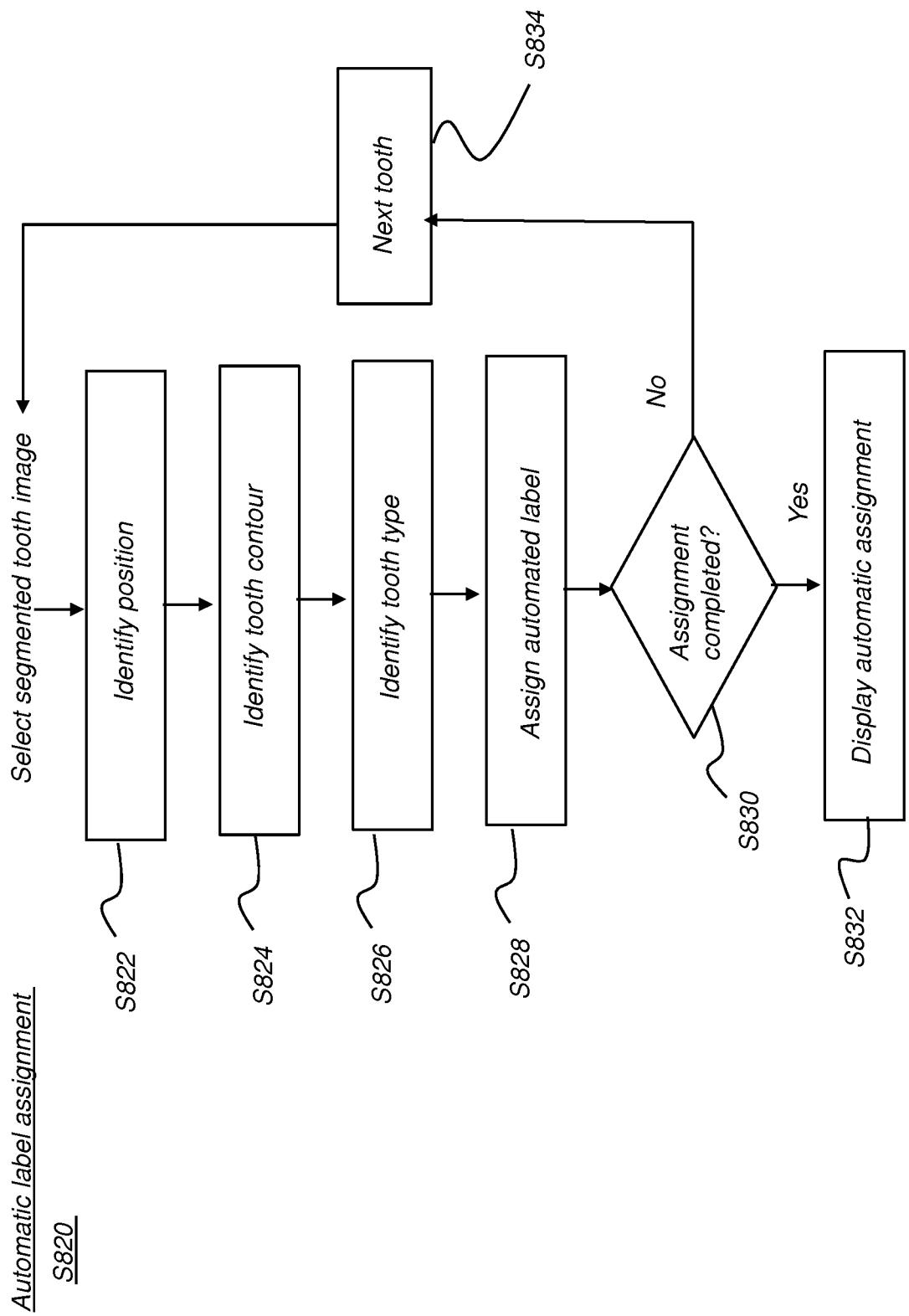
FIG. 14 is a logic flow diagram that shows detailed steps that can be used for automatic tooth label assignment.

FIG. 14 is a logic flow diagram that shows detailed steps that can be used for automatic tooth label assignment as part of step S820 (FIG. 13). Beginning with the segmented tooth image data, this sequence identifies various information about the tooth that can be used to properly characterize the tooth and assign a tooth number according to the specified numbering scheme. This sequence, represented by steps S824, S826, and S828 can be performed in any suitable order and can use any available data about the patient, including patient age, for example. Editing of automated results can be provided.

In the sequence of FIG. 14, a position identification step S822 detects the relative position of a subject tooth within the arch. Central teeth positions can be identified and used as reference for other teeth in the arch.

A tooth contour definition step S824 defines the contour of the tooth. This processing can use projection processing, in which the defined 3D contours are projected onto a 2D plane to form the 2D contours or outlines of the dental arch map. Projection can be performed in any of a number of ways. According to an embodiment of the present disclosure, the 3D cervical margin boundaries of the segmented teeth can be projected into the same reference (Z=0) plane. Based on the initial orientation of the tooth model, however, some projections could have artifacts, and projection in this manner may poorly represent the tooth outline. Alternately, a best plane that limits such artifacts can be determined, such as using the occlusal plane axis of the model or using the orientation axis of each tooth. For example, the axis of each tooth that maximizes the area of the projected contour can be identified. Weighting could be applied, with a higher weight assigned for incisors or other teeth based on factors such as ease of detection. Alternately, an axis that minimizes 2D tooth intersections between tooth outline boundaries can be used. The projection axis can alternately be adapted or modified, tooth by tooth, or according to tooth type (such as using a different projection axis for incisor, canine, premolar, and molar teeth). Manual editing of the cervical margin or other tooth contour definitions can also be performed as part of step S824.

Continuing with the FIG. 14 sequence, a tooth type identification step S826 then provides an identification of each tooth according to various metric and/or curvature characteristics.

The total number of teeth in the jaw can be one factor useful for tooth labeling. For each tooth, a number of features, individually or in combination, can be detected to help provide more accurate identification, including the following:

(i) crown axis;
(ii) mesio-distal axis;
(iii) mesial and distal points;
(iv) vestibular and lingual cusp; and/or
(v) grooves.

Automated detection of a class of each tooth as one of incisor, canine, premolar, or molar can be performed, based on aspects of tooth position, contour, and detected features. Following this, more precise determinations can be obtained, such as to distinguish permanent premolar from temporary molar, for example.

According to an exemplary embodiment of the present disclosure, computer learning algorithms are applied, such as for determining the number of a tooth according to various patient data, such as age and sex, and according to tooth characteristics, including the position, features, class detection, and/or other aspects described hereinabove.

Based on results from the analysis of steps S822, S824, and S826, an automated label assignment step S828 then assigns a number to each tooth. This automated assignment can be used for the tooth unless corrected, as was described previously with reference to the FIG. 13 sequence. A check step S830 determines whether or not all teeth in the arch, or region of interest within the arch, have been assigned a numeric label. Where all teeth have been assigned, a display step S832 shows the automated assignments. Where additional teeth need to be assigned a label, an iteration step S834 executes on a subsequent segmented tooth. Such additional teeth may include supernumerary teeth, for example.

Figure 15:
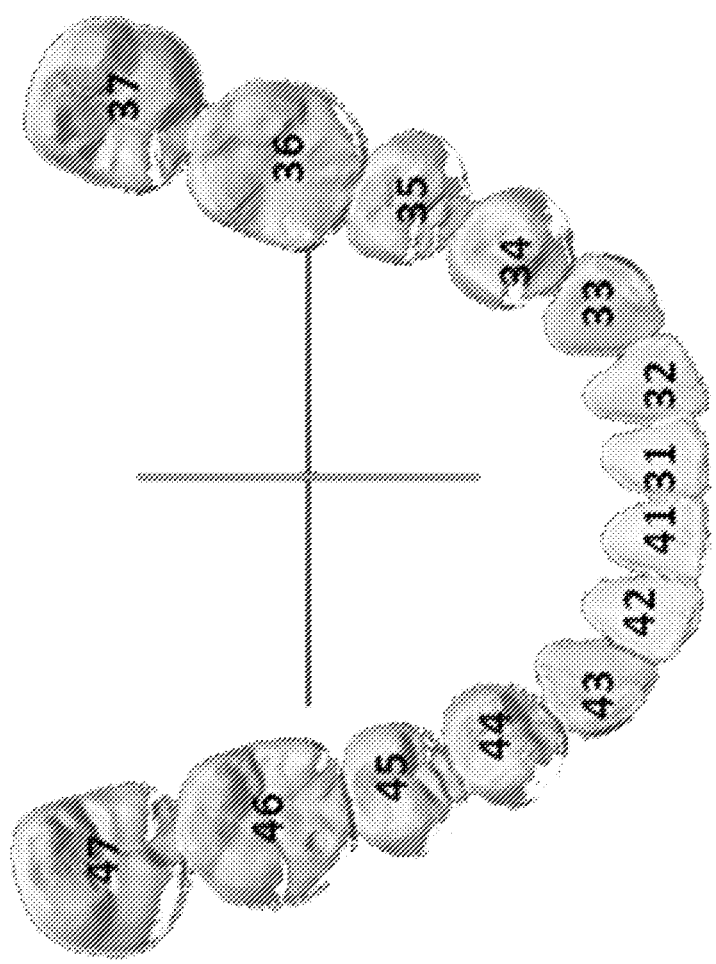
FIG. 15 is a diagram that shows an example of a displayed arch with numbered teeth.

FIG. 15 is a diagram that shows an example of a displayed arch with numbered teeth.

Figure 16:
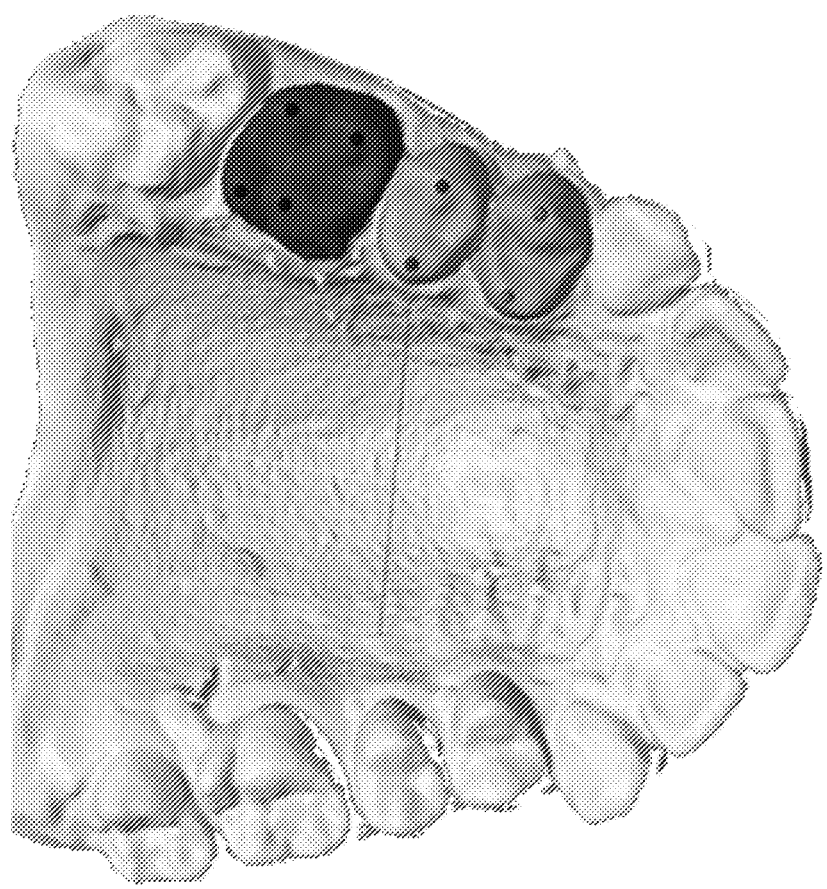
FIG. 16 shows a step in number assignment processing.

FIG. 16 shows a step in number assignment processing, whereby each tooth is assigned an automated label according to features such as relative position in the arch and tooth type, metrics, and other characteristics.

Another exemplary embodiment of the present disclosure can perform tooth labeling by detecting, e.g., initially, whether the dental arch is an upper arch (maxillary) or lower arch (mandibular). A procedure for making this determination can include, individually or in combination:

(i) determine the midline of the jaw. This can be determined using an oriented parabola that is traced through the tooth outline. The summit or point of inflection of the parabola can then be used to identify an initial position for the midline. This initial position can be refined using tooth symmetry nearest the position.

(ii) calculate and compare sizes for teeth centered about the midline. As identified by the inventors, teeth in the upper and lower jaws have characteristic size relationships that can be used to identify upper or lower arch. The determination of whether the teeth are in the upper/lower arch can be before or included in exemplary processes described related to FIG. 14.

In addition to upper/lower arch determination, a class of each tooth, for labeling, can be determined as one of incisor/canine/premolar/molar. Class of the tooth relates to relative position along the arch, which can be used to assign a "class probability" for class determination. Neighborhood probability can also be used to further enhance the likelihood of success in class determination. Among criteria that can also be used, individually or in combination, are the following:

(i) to distinguish incisors from canines, the characteristic shape of the border can be used;

(ii) to distinguish canines from premolar, the number and height of cusps can be used; and/or (iii) to distinguish premolars from molars, cusp features and tooth size can be used. The "class" of each tooth can be included in exemplary processes described related to FIG. 14.

Further, a determination of distance between adjacent teeth can be used to help determine whether or not a tooth is missing and can be before or included in exemplary processes described related to FIG. 14.

The analysis for arch identification and tooth class can also be helpful for determining if a tooth is permanent or deciduous. Age and sex of the patient can also be used to determine whether or not a tooth is permanent, along with factors such as overall tooth size, length, and width, length-to-width ratio. Cusp shape and the distribution of maximum and minimum curvatures can also be helpful for making the decision as to whether a tooth is permanent or temporary.

The total number of teeth in the jaw and their relative distribution can also help to determine the age of the patient, if not specifically provided as an input used with exemplary processes of FIG. 14, and can be a factor in determining if a tooth is permanent. A reference database of tooth data can alternately be used, for providing various metrics and characteristics.

A combination of factors can be used to help make an appropriate decision as to tooth numbering. Factors, individually or in combination, can include age and sex of the patient, probable tooth class, relative tooth position, associated upper or lower jaw, and permanent or deciduous status.

Because it uses 3D volume information acquired from the patient, the dental arch map of the present disclosure can be more accurate for planning and tracking individual progress than are conventional dental arch mapping tools. The dental arch numbering that is generated using the sequence of FIGS. 13 and 14 can be used for forming a treatment plan and for accurately recording and communicating treatment data. According to an embodiment of the present disclosure, the individual tooth outlines provided on the dynamic dental arch map can serve as indices for access to additional images and annotation for the teeth. Thus, for example, selecting a particular tooth on the display can enable selective display of images of the tooth as well as records and annotation for previous or planned treatment of the tooth.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as host processor 120 as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can provide dental arch maps correlated to 3D virtual models of a patient's dentition. Exemplary embodiments according to the application can include various features described herein (individually or in combination). In one embodiment, operations described with respect to FIGS. 8B-10 can partially implement steps S150 and 160. Although embodiments of the present disclosure are illustrated using dental imaging apparatus, similar principles can be applied for other types of diagnostic imaging and for other anatomy.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

What is claimed is:

1. A method for automatically assigning numeric labels to teeth in a dental arch map comprising:
   providing a segmented 3D surface image of patient dentition comprising 3D contours of identified individual teeth and determined tooth position in a dental arch for each of the identified individual teeth;
   identifying a 2D plane based at least in part on: an occlusal plane axis of the segmented 3D surface image or an orientation axis of one or more of the identified individual teeth;
   projecting the 3D contours of the identified individual teeth along the 2D plane to define a tooth contour for each of the identified individual teeth in the 2D plane;
   identifying a tooth type as one of incisor, canine, premolar, or molar for each of the identified individual teeth;
   labeling a display of the tooth contour in the 2D plane with an assigned tooth number according to the tooth position, tooth contour, and tooth type for each of the identified individual teeth; and
   displaying the labeled mapping.

2. The method of claim 1 further comprising editing the assigned tooth number for at least one of the identified individual teeth according to an operator instruction.

3. The method of claim 1 further comprising acquiring a 3D surface image of patient dentition.

4. The method of claim 3 wherein the 3D surface image is from a cone beam computed tomography apparatus.

5. The method of claim 3 wherein the 3D surface image is from a structured light imaging apparatus.

6. The method of claim 3 wherein the 3D surface image is from an ultrasound apparatus.

7. The method of claim 6 wherein segmenting the 3D surface image comprises using one or more of snake-based segmentation, iterative segmentation techniques, and region growing segmentation.

8. The method of claim 3 further comprising segmenting the 3D surface image to identify individual teeth and to determine tooth position in the dental arch for each of the individual teeth.

9. The method of claim 1 further comprising accepting and executing an operator instruction that corrects the segmented 3D surface image for one or more of the identified individual teeth.

10. The method of claim 1 further comprising accepting and executing an operator instruction that corrects the identified tooth type for one or more of the identified individual teeth.

11. The method of claim 1 wherein the assigned tooth number conforms to one or more of Universal numbering, ISO numbering, and Palmer numbering notation.

12. The method of claim 1 wherein the assigned tooth number is determined using computer learning algorithms based on various patient data and tooth characteristics.

13. The method of claim 1 further comprising accepting an operator instruction entered by selecting a displayed contour for a tooth.

14. A dental imaging apparatus comprising:
   a surface imaging apparatus that acquires a 3D surface image of a patient dentition;
   a host processor that is configured to respond to operator instructions to:
      segment the 3D surface image to identify 3D contours of individual teeth in a dental arch,
      identify a 2D plane based at least in part on: an occlusal plane axis of the 3D surface image or an orientation axis of one or more of the individual teeth;
      project the 3D contours of the individual teeth along the 2D plane to form a 2D mapping of tooth outlines for the individual teeth in the dental arch in the 2D plane,
      identify the tooth type as one of incisor, canine, premolar, or molar for each of the individual teeth, and
      label the 2D mapping of tooth outlines in the 2D plane with a numbering scheme according to at least tooth position, individual tooth contour, and tooth type for each of the individual teeth in the dental arch; and a display in signal communication with the host processor for displaying the tooth labeling.

15. The dental imaging apparatus of claim 14 wherein the surface imaging apparatus uses structured reflectance light.

16. The dental imaging apparatus of claim 14 wherein the surface imaging apparatus is a cone beam computed tomography imaging apparatus.

17. The dental imaging apparatus of claim 14 wherein the surface imaging apparatus is an optical coherence tomography apparatus.

18. A method for automatically assigning a numeric label to a tooth in a dental arch map, the method executed at least in part by a computer and comprising:

acquiring a 3D surface image of patient dentition;

segmenting the 3D surface image content to identify 3D contours of individual teeth and to determine a tooth position for each of the individual teeth in a dental arch;

identifying a 2D plane based at least in part on: an occlusal plane axis of the 3D surface image or an orientation axis of one or more of the identified individual teeth;

projecting the 3D contours of the individual teeth along the 2D plane to define a 2D tooth contour for each of the individual teeth in a 2D mapping on the 2D plane;

identifying a tooth type according to one or more of the tooth position and the 2D tooth contour for each of the individual teeth;

labeling a display showing the 2D tooth contour in the 2D plane with an assigned tooth number according to the tooth position, tooth contour, and identified tooth type within the 2D mapping for each of the individual teeth; and displaying the labeled mapping.

19. The method of claim 18 wherein identifying the tooth type comprises identifying a tooth as one of incisor, canine, premolar, or molar type.

20. The method of claim 18 wherein identifying the tooth type comprises identifying a tooth as a supernumerary tooth.

* * * * *